US012599638B2

(12) United States Patent
Yoshitake et al.

(10) Patent No.: US 12,599,638 B2
(45) Date of Patent: Apr. 14, 2026

(54) FEED AND COMPOSITION COMPRISING LACTIC ACID BACTERIA AND FATTY ACID

(71) Applicant: HOUSE WELLNESS FOODS CORPORATION, Hyogo (JP)

(72) Inventors: Rieko Yoshitake, Hyogo (JP); Tsubasa Nakajima, Hyogo (JP); Yoshitaka Hirose, Hyogo (JP); Mika Yamaguchi, Hyogo (JP)

(73) Assignee: HOUSE WELLNESS FOODS CORPORATION, Hyogo (JP)

( * ) Notice: Subject to any disclaimer, the term of this patent is extended or adjusted under 35 U.S.C. 154(b) by 373 days.

(21) Appl. No.: 18/026,464

(22) PCT Filed: Sep. 21, 2021

(86) PCT No.: PCT/JP2021/034480
§ 371 (c)(1),
(2) Date: Mar. 15, 2023

(87) PCT Pub. No.: WO2022/065268
PCT Pub. Date: Mar. 31, 2022

(65) Prior Publication Data
US 2023/0346858 A1     Nov. 2, 2023

(30) Foreign Application Priority Data

Sep. 25, 2020     (JP) ................................. 2020-161335

(51) Int. Cl.
A23K 20/158          (2016.01)
A23K 10/16          (2016.01)
(Continued)

(52) U.S. Cl.
CPC ............ A61K 35/747 (2013.01); A23K 10/16 (2016.05); A23K 20/158 (2016.05); A61K 31/19 (2013.01);
(Continued)

(58) Field of Classification Search
CPC .... A61K 35/747; A61K 31/19; A61K 35/744; A23K 10/16; A23K 20/158; A23K 10/18;
(Continued)

(56) References Cited

U.S. PATENT DOCUMENTS

2013/0302380 A1    11/2013   Fujiwara et al.
2014/0234379 A1     8/2014   Fujiwara et al.
(Continued)

FOREIGN PATENT DOCUMENTS

CN          107950792          4/2018
CN          110881576          3/2020
(Continued)

OTHER PUBLICATIONS

Machine Translation of WO 2004084923 A1; Original Document Published Oct. 7, 2004 (Year: 2004).*
(Continued)

*Primary Examiner* — Robert B Mondesi
(74) *Attorney, Agent, or Firm* — Wenderoth, Lind & Ponack, L.L.P.

(57)          ABSTRACT

A problem to be solved by the present invention is to provide one or more selected from (1) a feed comprising *Lactobacillus plantarum* strain L-137 or a processed product thereof and a fatty acid or a salt thereof, (2) a composition for enhancing IL-12 production, comprising *Lactobacillus plantarum* strain L-137 or a processed product thereof and a fatty acid or a salt thereof, (3) a composition for immunostimulation, comprising *Lactobacillus plantarum* strain L-137 or a processed product thereof and a fatty acid or a salt thereof, and (4) a composition for bacteriostasis, comprising *Lactobacillus plantarum* strain L-137 or a processed product thereof and a fatty acid or a salt thereof. The problem is
(Continued)

solved by providing one or more of the feed or the compositions.

7 Claims, 1 Drawing Sheet

Specification includes a Sequence Listing.

(51) Int. Cl.

| | |
|---|---|
| *A61K 31/19* | (2006.01) |
| *A61K 35/747* | (2015.01) |
| *A61P 31/04* | (2006.01) |
| *A61P 37/04* | (2006.01) |
| *C12R 1/25* | (2006.01) |

(52) U.S. Cl.
CPC ............... *A61P 31/04* (2018.01); *A61P 37/04* (2018.01); *C12R 2001/25* (2021.05)

(58) Field of Classification Search
CPC .......... A23K 50/75; A61P 31/04; A61P 37/04; C12R 2001/25; A23C 9/1234; A23V 2400/169; A23L 2/52; A23L 33/12; A23L 33/135; A23L 2/38; C12N 1/20; C12N 1/205
USPC ....................................................... 424/93.45
See application file for complete search history.

(56) References Cited

U.S. PATENT DOCUMENTS

| | | | |
|---|---|---|---|
| 2017/0106028 A1 | 4/2017 | Fujiwara et al. | |
| 2019/0192584 A1 | 6/2019 | Fujiwara et al. | |
| 2022/0105140 A1 | 4/2022 | Fujiwara et al. | |

FOREIGN PATENT DOCUMENTS

| | | | | |
|---|---|---|---|---|
| EP | 2 177 110 | 4/2010 | | |
| EP | 2 659 898 | 11/2013 | | |
| JP | 2001-64174 | 3/2001 | | |
| JP | 2002-80364 | 3/2002 | | |
| JP | 2005-21156 | 1/2005 | | |
| JP | 2005-68092 | 3/2005 | | |
| JP | 2006-76961 | 3/2006 | | |
| JP | 2008-61513 | 3/2008 | | |
| JP | 2008-195713 | 8/2008 | | |
| JP | 2009-57344 | 3/2009 | | |
| JP | 2010-6801 | 1/2010 | | |
| JP | 2010-95465 | 4/2010 | | |
| JP | 2017-201984 | 11/2017 | | |
| JP | 2018-50488 | 4/2018 | | |
| JP | 2019-198314 | 11/2019 | | |
| JP | 2022-551972 | 6/2023 | | |
| KR | 10-2059623 | 12/2019 | | |
| WO | 2004/084922 | 10/2004 | | |
| WO | 2004/084923 | 10/2004 | | |
| WO | WO-2004084923 | A1 * | 10/2004 | ............. A23K 10/16 |
| WO | 2019/118843 | 6/2019 | | |

OTHER PUBLICATIONS

Fu, W. and Mathews, A.P. (1999) Lactic acid production from lactose by Lactobacillus plantarum: kinetic model and effects of pH, substrate and oxygen. Biochemical Engineering Journal 3, 163-170. DOI: 10.1016/s1369-703x(99)00014-5 (Year: 1999).*
Communication pursuant to Rule 114(2) EPC dated Jul. 3, 2024 in European Patent Application No. 21872397.1.
Roghieh Safari, et al., Apple cider vinegar boosted immunomodulatory and health promoting effects of *Lactobacillus casei* in common carp (*Cyprinus carpio*, Fish & Shellfish Immunology, 67, 2017, pp. 441-448.

Tadao Saito et al., "Encyclopedia of Yoghurt", Apr. 20, 2016, pp. 86-95, with English Translation.
"Tables of Food Composition", 2016, pp. 1-12, with Partial English Translation.
"SPL-M100 Application Note", AiSTI Science Co., Ltd., pp. 1-8, with Partial English Translation.
Rumi Kaji, et al., "Bacterial Teichoic Acids Reverse Predominant IL-12 Production Induced by Certain *Lactobacillus* Strains into Predominant IL-10 Production via TLR2-Dependent ERK Activation in Macrophages", J Immunol, 2010, 184 (7):3505-3513.
J. Gary Wheeler, et al., "Impact of Dietary Yogurt on Immune Function", The American Journal of the Medical Sciences, vol. 313, Issue 2, Jan. 1997, pp. 120-123.
"Tables of Food Composition", 2018, with Partial English Translation.
Naoki Morita, et al., "Gut immunity activation by lactic acid and pyruvic acid formed by gut microbiota", Biochemistry, vol. 92, No. 2, pp. 231-235, 2020.
News Release, B Food Science Co., Ltd., May 21, 2019, pp. 1-3, with Partial English Translation.
Data from the German Bundeslebensmittelschlüssel, pp. 1-8, with English version.
Dataset by McCane and Widdowson, McCance_Widdowsons_Composition_of_Foods_Integrated_Dataset_2021, https://www.gov.uk/government/publications/composition-of-foods-integrated-dataset-cofid. sheets 1.8 (SFA per 100gFood) and 1.10 (MUFA per 100gFood).
Extended European Search Report issued Sep. 24, 2024 in European Patent Application No. 21872397.1.
Najla Haddaji, et al., "Effect of environmental stress on cell surface and membrane fatty acids of *Lactobacillus plantarum*", Arch Microbiol (2017) 199:1243-1250.
Shigeaki Inoue, et al., "Fermentation of non-sterilized fish biomass with a mixed culture of film-forming yeasts and lactobacilli and its effect on innate and adaptive immunity in mice", Journal of Bioscience and Bioengineering, vol. 116, No. 6, 682-687, 2013.
D. Pantoflickova, et al., "Favourable effect of regular intake of fermented milk containing Lactobacillus johnsonii on Helicobacter pylori associated gastritis", Aliment Pharmacol Ther, 2003, 18: 805-813.
Susana Vargas Muñoz, et al., "Transformation kinetics of fermented milk using Lactobacillus casei (Lc1) and *Streptococcus thermophilus*: comparison of results with other Inocula", Journal of Dairy Research, 2017, 84 102-108.
D. Derewiaka, et al., "Chia seed oil as an additive to yogurt", Grasas Y Aceites, 70(2), Apr.-Jun. 2019, e302, ISSN-L: 0017-3495.
Heping Zhang et al., "Handbook of Modern Dairy Industry", published by China Light Industry Press, 1st edition, 1st printing (Aug. 2005), p. 1064, with partial English translation.
International Preliminary Report on Patentability and Written Opinion of the International Searching Authority issued Mar. 28, 2023 in International (PCT) Application No. PCT/JP2021/034480.
International Search Report (ISR) issued Nov. 22, 2021 in International (PCT) Application No. PCT/JP2021/034480.
Asarat, M., et al. "Short-chain fatty acids produced by synbiotic mixtures in skim milk differentially regulate proliferation and cytokine production in peripheral blood mononuclear cells", International Journal of Food Sciences and Nutrition, 2015, vol. 66, No. 7, p. 755-765.
Vinolo, M. A. R., et al., "Regulation of Inflammation by Short Chain Fatty Acids", Nutrients, 2011, vol. 3, pp. 858-876.
Dark chocolate (85%), FDA, Nutrition Information Database (New Edition), pp. 1-15, with English-language Translation; https://consumer.fda.gov.tw//Food/tfndDetail.aspx?nodeID=178&f=0&id=1936; 2017 Taiwan Food and Drug Administration, Ministry of Health and Welfare.
Full-fat curd fermented milk, FDA, Nutrition Information Database (New Edition), pp. 1-13, with English-language Translation; https://consumer.fda.gov.tw/Food/tfndDetail.aspx?nodeID=178&f=0&id=1381; 2017 Taiwan Food and Drug Administration, Ministry of Health and Welfare.

* cited by examiner

```
                          SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
tgtctcacct gctatttgcc ttac                                          24

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
catacacatt ctctctaagt ttccactgt                                     29

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cctctctggc aaagtccaag                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
catctgccca tttgatgttg                                               20
```

FEED AND COMPOSITION COMPRISING LACTIC ACID BACTERIA AND FATTY ACID

TECHNICAL FIELD

The present invention relates to a feed and a composition each comprising a combination of specific lactic acid bacteria or a processed product thereof and a fatty acid or a salt thereof.

BACKGROUND ART

Interleukin 12 (IL-12) is a cytokine secreted by activated phagocytes and dendritic cells and plays an important role in the pathogenesis of various immune-mediated diseases. Certain types of lactic acid bacteria are known to have an immunostimulatory effect and an IL-12 production promoting effect (Patent literature 1).

CITATION LIST

Patent Literature

Patent literature 1: JP 2010-6801 A

SUMMARY OF INVENTION

Technical Problem

So far there is no report that, when combined with a fatty acid or a salt thereof, the lactic acid bacteria *Lactobacillus plantarum* strain L-137 (*Lactobacillus plantarum* L-137) or a processed product thereof exhibits an enhanced IL-12 production promoting effect and/or an enhanced immunostimulatory effect, and also exhibits a bacteriostatic effect. Use of this combination for a feed has also not been reported.

An object of the present invention is to provide one or more selected from (1) a feed comprising *Lactobacillus plantarum* strain L-137 or a processed product thereof and a fatty acid or a salt thereof, (2) a composition for enhancing IL-12 production, comprising *Lactobacillus plantarum* strain L-137 or a processed product thereof and a fatty acid or a salt thereof, (3) a composition for immunostimulation, comprising *Lactobacillus plantarum* strain L-137 or a processed product thereof and a fatty acid or a salt thereof, and (4) a composition for bacteriostasis, comprising *Lactobacillus plantarum* strain L-137 or a processed product thereof and a fatty acid or a salt thereof.

Solution to Problem

The inventors found that, when combined with a fatty acid or a salt thereof, the lactic acid bacteria *Lactobacillus plantarum* strain L-137 or a processed product thereof exhibits an enhanced IL-12 production promoting effect and an enhanced immunostimulatory effect, and also exhibits a bacteriostatic effect. The inventors also found that this combination is suitable for preparation of a feed or a composition. The inventors further found that *Lactobacillus plantarum* strain L-137 is more effective than other lactic acid bacteria when used in combination with a fatty acid or a salt thereof. The inventors carried out further studies and completed the present invention.

That is, the present invention includes the following.

(1) A feed comprising *Lactobacillus plantarum* strain L-137 (*Lactobacillus plantarum* L-137) or a processed product thereof and a fatty acid or a salt thereof.

(2) The feed according to the above (1), wherein the fatty acid is at least one selected from the group consisting of a short-chain fatty acid, a medium-chain fatty acid and a long-chain fatty acid, or a mixture thereof.

(3) The feed according to the above (2), wherein the short-chain fatty acid is at least one selected from the group consisting of formic acid, acetic acid, propionic acid, butyric acid, isobutyric acid, valeric acid, isovaleric acid, lactic acid, pyruvic acid, caproic acid and succinic acid.

(4) The feed according to any one of the above (1) to (3), wherein cells of the *Lactobacillus plantarum* strain L-137 are killed bacterial cells.

(5) The feed according to any one of the above (1) to (4), wherein the amount of the *Lactobacillus plantarum* strain L-137 or a processed product thereof contained in the feed is 0.0001 to 0.1% by mass relative to the total mass of the feed.

(6) The feed according to any one of the above (1) to (5), wherein the mass ratio of the *Lactobacillus plantarum* strain L-137 or a processed product thereof to the fatty acid or a salt thereof in the feed is 1:0.5 to 50000.

(7) A composition for enhancing IL-12 production, comprising *Lactobacillus plantarum* strain L-137 (*Lactobacillus plantarum* L-137) or a processed product thereof and a fatty acid or a salt thereof.

(8) A composition for immunostimulation, comprising *Lactobacillus plantarum* strain L-137 (*Lactobacillus plantarum* L-137) or a processed product thereof and a fatty acid or a salt thereof.

(9) A composition for bacteriostasis, comprising *Lactobacillus plantarum* strain L-137 (*Lactobacillus plantarum* L-137) or a processed product thereof and a fatty acid or a salt thereof.

(10) A composition comprising *Lactobacillus plantarum* strain L-137 (*Lactobacillus plantarum* L-137) or a processed product thereof and a fatty acid or a salt thereof.

(11) A composition for immunostimulation, comprising lactic acid bacteria or a processed product thereof and a fatty acid or a salt thereof.

(12) The composition according to the above (11), which is a medicament, a veterinary medicine, a quasi-drug, a feed, a food or a drink, or a food or drink additive.

Advantageous Effects of Invention

The present disclosure preferably provides one or more selected from (1) a feed comprising *Lactobacillus plantarum* strain L-137 or a processed product thereof and a fatty acid or a salt thereof, (2) a composition for enhancing IL-12 production, comprising *Lactobacillus plantarum* strain L-137 or a processed product thereof and a fatty acid or a salt thereof, (3) a composition for immunostimulation, comprising *Lactobacillus plantarum* strain L-137 or a processed product thereof and a fatty acid or a salt thereof, and (4) a composition for bacteriostasis, comprising *Lactobacillus plantarum* strain L-137 or a processed product thereof and a fatty acid or a salt thereof.

DESCRIPTION OF EMBODIMENTS

Figure 1:
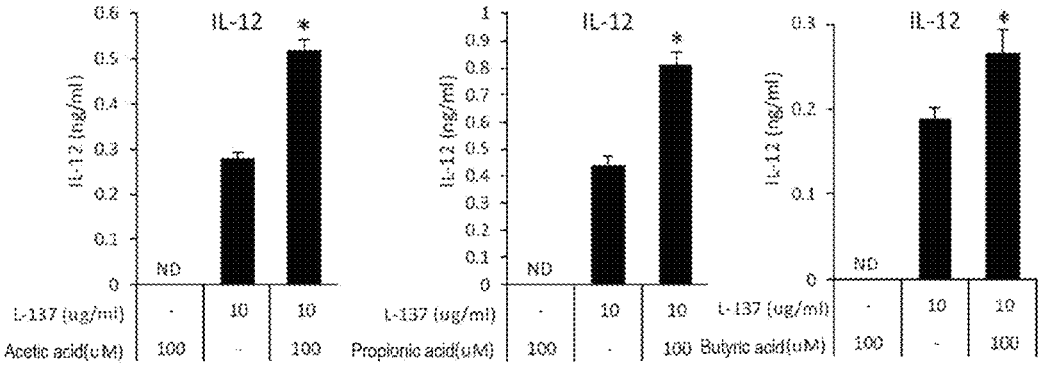
FIG. 1 shows the production of IL-12 by an immune cell line that received the lactic acid bacteria of the present invention alone, a fatty acid (a short-chain fatty acid) or a salt thereof alone, or a combination of the lactic acid bacteria and the fatty acid or a salt thereof. The asterisks (*) in the charts indicate that the p value of t-test between the addition of the lactic acid bacteria L-137 alone and the co-addition of the lactic acid bacteria L-137 and the fatty acid was $0.01 \leq p < 0.05$.

Lactic Acid Bacteria *Lactobacillus plantarum* Strain L-137

The lactic acid bacteria *Lactobacillus plantarum* strain L-137 (*Lactobacillus plantarum* L-137) used in the present invention were deposited with the International Patent Organism Depositary of the Incorporated Administrative Agency National Institute of Advanced Industrial Science and Technology (currently known as the International Patent Organism Depositary of the Incorporated Administrative Agency National Institute of Technology and Evaluation; address: #120, 2-5-8 Kazusakamatari, Kisarazu-shi, Chiba 292-0818, Japan) under Accession No. FERM BP-08607 (transferred from FERM P-15317 deposited on Nov. 30, 1995). *Lactobacillus plantarum* L-137 herein includes mutants of *Lactobacillus plantarum* L-137 that have the same characteristics as those of *Lactobacillus plantarum* L-137.

Other lactic acid bacteria, in particular, other lactic acid bacteria having an immunostimulatory effect can be used herein instead of or together with the *Lactobacillus plantarum* strain L-137.

The *Lactobacillus plantarum* strain L-137 may be those cultured in a culture medium such as a natural medium, a synthetic medium and a semi-synthetic medium. The culture of the lactic acid bacteria herein may be performed in accordance with a known method, a method known per se or an equivalent method thereof.

The culture medium can be any culture medium, and is preferably, for example, a culture medium containing a nitrogen source and/or a carbon source. The nitrogen source may be, for example, but is not limited to, meat extract, peptone, gluten, casein, yeast extract, amino acids, etc. The carbon source may be, for example, but is not limited to, glucose, xylose, fructose, inositol, maltose, starch syrup, yeast extract, starch, bagasse, wheat bran, molasses, glycerol, etc. These can be used alone or in combination of two or more types.

The culture medium can further contain a mineral in addition to the nitrogen source and/or the carbon source. The mineral may be, for example, but is not limited to, ammonium sulfate, potassium phosphate, magnesium chloride, sodium chloride, iron, manganese, molybdenum, various types of vitamins, etc. These can be used alone or in combination of two or more types.

The culture temperature and time of the lactic acid bacteria *Lactobacillus plantarum* strain L-137 may be any temperature and time that allow the bacteria to be efficiently cultured. In an embodiment of the present invention, the culture temperature may be, for example, typically about 25 to 40° C., preferably about 27 to 35° C., and the culture time may be, for example, about 12 to 48 hours. In an embodiment of the present invention, the lactic acid bacteria may be cultured with aeration and shaking. The pH of the culture medium is not particularly limited, and in an embodiment of the present invention, the pH may typically be about 3 to 6, preferably about 4 to 6.

Processed Products of Lactic Acid Bacteria *Lactobacillus plantarum* Strain L-137

A "processed product" of the lactic acid bacteria *Lactobacillus plantarum* strain L-137 is preferably, but not limited to, a processed product or a culture of the lactic acid bacteria. The lactic acid bacteria may be viable bacterial cells or killed bacterial cells, but killed bacterial cells are preferred due to stability, ease of handling, and other advantages.

The processed product may directly be used, or may be formed into a powder by lyophilization, low-temperature drying, spray drying, L-drying, or a combination thereof, according to the present invention. The processed product (culture) may be diluted in an appropriate solvent (water, an alcohol, an organic solvent, etc.), or may be formed into a gel or a solid preparation by addition of an appropriate additive.

Preparation methods for killed cells of the lactic acid bacteria will be specifically described below.

The preparation methods for the killed bacterial cells may be any methods that do not impair the effects of the present invention. The killed bacterial cells may be prepared by, for example, (I) a method involving separating viable cells of the lactic acid bacteria from a liquid medium at the end of culture, and performing sterilization to kill the viable bacterial cells to give killed bacterial cells, or (II) a method involving sterilizing a liquid medium containing viable cells of the lactic acid bacteria to kill the viable bacterial cells, and separating the killed bacterial cells from the liquid medium.

The separation method of the bacterial cells from a liquid medium may be done by any method usually employed in this field. Specifically, in an embodiment of the present invention, the bacterial cells may be separated from a liquid medium by, for example, adding distilled water to the liquid medium, and removing the supernatant by centrifugation etc. In this embodiment, if desired, after the addition of distilled water to the liquid medium and the centrifugation for removal of the supernatant, distilled water may be added to the residue obtained by the removal of the supernatant and the resulting suspension may be further centrifuged, and this procedure may be repeated several times. In an embodiment of the present invention, the separation procedure may include filtration.

The sterilization method to kill the viable cells of the lactic acid bacteria will be specifically described below. The sterilization method is not particularly limited, and the sterilization may be performed by, for example, heating, UV irradiation, formalin treatment, etc. The sterilization may be performed on harvested viable bacterial cells or on a liquid medium containing viable bacterial cells.

When the sterilization is performed by heating, the heating temperature may be, for example, but is not limited to, typically about 60 to 100° C., preferably about 70 to 90° C.

The heating means may be those known in the art, and may be, for example, but is not limited to, a heater etc. The heating time may be any length of time that allows sterilization to be sufficiently complete, and heating may be performed, for example, typically for about 5 to 40 minutes, preferably for about 10 to 30 minutes, after the temperature reaches a desired level.

The killed bacterial cells prepared as above may be subjected to grinding, disruption or lyophilization to give processed killed bacterial cells. In the present invention, such processed killed bacterial cells are also suitable as killed bacterial cells.

An extract of the lactic acid bacterial cells may be used instead of or together with the bacterial cells, according to the present invention. The extraction method for obtaining the extract is not particularly limited, and the extraction may be performed by a known method, a method known per se or an equivalent method thereof. Specifically, the extraction may be performed by, for example, (i) a method involving adding viable or killed cells of the lactic acid bacteria to an extraction solvent at room temperature or an elevated temperature under normal or elevated pressure, and performing extraction by immersion or agitation, or (ii) a method involving adding viable or killed cells of the lactic acid bacteria to an extraction solvent, and performing extraction by refluxing. The extraction temperature and time and the type of extraction solvent used may be selected as appropriate depending on the extraction conditions.

The extraction solvent may be, for example, but is not limited to, water, an organic solvent, or a mixed solvent thereof at any mixing ratio. The organic solvent may be, for example, but is not limited to, alcohols that are liquid at room temperature, such as lower alcohols (e.g., methanol, ethanol, n-propanol, isopropanol, n-butanol, etc.) and poly-alcohols (e.g., 1,3-butylene glycol, propylene glycol, glycerol, etc.); ethers (e.g., diethyl ether, propyl ether, etc.); esters (e.g., ethyl acetate, butyl acetate, etc.); ketones (e.g., acetone, ethyl methyl ketone, etc.); hydrocarbons (e.g., hexane, xylene, toluene, etc.); chloroform; etc. These may be used alone or in combination of two or more types. Of these organic solvents, alcohols that are liquid at room temperature, such as lower alcohols of 1 to 4 carbon atoms, are preferred in terms of operability, environmental impact, etc. Ethanol is more preferred in terms of safety concerns over a residual solvent.

If desired, a mixture containing the extract and the residue obtained by the above extraction procedure may be filtered or centrifuged to remove the residual solid material, and the resulting extract may be directly used for the preparation of the carrier of the present invention, or alternatively may be dried and/or powdered by concentration, lyophilization, spray-drying, or other methods and then used for the preparation of the carrier of the present invention.

The amount of the lactic acid bacteria or a processed product thereof in the feed or composition of the present invention may be any amount as long as the effects of the present invention are not impaired, and may be, for example, about 0.0001 to 0.1% by mass, preferably 0.001 to 0.01% by mass, relative to 100% by mass of the feed or composition. The mass ratio of the lactic acid bacteria or a processed product thereof to the fatty acid or a salt thereof in the feed or composition of the present invention may be any ratio as long as the effects of the present invention are not impaired, and may be 1:0.5 to 50000, preferably 1:0.5 to 2000, more preferably 1:0.5 to 100, particularly preferably 1:0.5 to 2.5.

Fatty Acids

The fatty acid used herein may be, for example, a straight- or branched-chain saturated or unsaturated fatty acid. Specific examples of such a fatty acid include formic acid, acetic acid, propionic acid, butyric acid, valeric acid, caproic acid, enanthic acid, caprylic acid, pelargonic acid, capric acid, lauric acid, myristic acid, pentadecylic acid, palmitic acid, palmitoleic acid, margaric acid, stearic acid, tuberculostearic acid, isostearic acid, oleic acid, elaidic acid, vaccenic acid, linoleic acid, α-linolenic acid, γ-linolenic acid, eleostearic acid, stearidonic acid, ricinoleic acid, arachidic acid, arachidonic acid, dihomo-γ-linolenic acid, eicosapentaenoic acid, behenic acid, erucic acid, docosapentaenoic acid, docosahexaenoic acid, lignoceric acid, nervonic acid, cerotic acid, montanic acid, melissic acid, malonic acid, succinic acid, malic acid, citric acid, glutaric acid, adipic acid, pimelic acid, suberic acid, azelaic acid, sebacic acid, etc.

A preferred fatty acid may include at least one selected from the group consisting of a short-chain fatty acid, a medium-chain fatty acid and a long-chain fatty acid, or a mixture thereof. More preferably, the fatty acid is a short-chain fatty acid or a medium-chain fatty acid, and is further preferably a short-chain fatty acid.

The fatty acid may have a substituent. The substituent may typically be a known group or bond used in the field of pharmaceuticals, veterinary medicines, foods, cosmetics, etc., including, for example, but not limited to, an alkyl group, a cycloalkyl group, an alkoxy group, a carboxyl group, a ketone group, an aldehyde group, a carbonyl group, a hydroxyl group, a nitro group, an amino group, a cyano group, a thiol group, a nitro group, an ether bond, an ester bond, an amide bond, a urethane bond, etc.

The fatty acid used in the present invention may be an animal- or vegetable-derived free fatty acid obtained by a known method or a method known per se, preferably from, for example, soybean oil, rapeseed oil, cottonseed oil, peanut oil, palm oil, sunflower oil, wheat germ oil, rice bran oil, corn oil, sesame oil, cherry seed oil, safflower oil, linseed oil, almond nut oil, inca inchi oil, sesame oil, olive oil, orange seed oil, pumpkin seed oil, perilla oil, tea seed oil, camellia oil, peanut oil, grape seed oil, macadamia nut oil, beef tallow, lard, egg yolk oil; a fish oil obtained from sardine, salmon, mackerel, Pacific saury, herring or tuna; a liver oil obtained from squid or Alaska pollack; a bonito or tuna orbital oil; seal oil; krill oil; etc. The fatty acid of the present invention may also be a commercially available fatty acid produced by chemical synthesis, etc.

Salts of Fatty Acids

The fatty acid used herein can be converted into a desired salt in accordance with a known method. Preferred examples of such a salt include, but are not limited to, a salt with an inorganic base, such as sodium, potassium, lithium, calcium or magnesium; a salt with an organic compound, such as ammonia, dimethylamine, trimethylamine or dicyclohexylamine; etc.

Short-Chain Fatty Acids

The short-chain fatty acid used herein is typically a straight- or branched-chain saturated or unsaturated fatty acid of 1 to 6 carbon atoms. Preferred examples of the short-chain fatty acid include, but are not limited to, for example, formic acid, acetic acid, propionic acid, butyric acid, isobutyric acid, isovaleric acid, lactic acid, pyruvic acid, valeric acid, caproic acid, succinic acid, fumaric acid, maleic acid, malic acid, citric acid, etc. More preferred examples of the short-chain fatty acid include, but are not limited to, formic acid, acetic acid, propionic acid, butyric acid, isobutyric acid, isovaleric acid, lactic acid, pyruvic acid, valeric acid, caproic acid and succinic acid. Further preferred examples of the short-chain fatty acid include, but are not limited to, acetic acid, propionic acid and butyric acid.

In another preferred example, the short-chain fatty acid is used in the form of a salt. The salt of the short-chain fatty acid may be a salt with an inorganic base as exemplified above, and is more preferably a salt with sodium, potassium, calcium, etc.

Medium-Chain Fatty Acids

The medium-chain fatty acid used herein is typically a straight- or branched-chain saturated or unsaturated fatty acid of 7 to 11 carbon atoms. Preferred examples of the medium-chain fatty acid include, for example, decanoic acid (capric acid), enanthic acid, caprylic acid, pelargonic acid, etc. Preferably, the medium-chain fatty acid is a straight-chain fatty acid or a saturated fatty acid, and is more preferably a straight-chain saturated fatty acid.

Long-Chain Fatty Acids

The long-chain fatty acid used herein is typically a straight- or branched-chain saturated or unsaturated fatty acid of 12 carbon atoms or more. Preferred examples of the long-chain fatty acid include, for example, lauric acid, tridecyl acid, myristic acid, palmitic acid, stearic acid, palmitoleic acid, vaccenic acid, paullinic acid, linoleic acid, γ-linolenic acid, α-linolenic acid, arachidonic acid, oleic acid, etc. Preferably, the long-chain fatty acid is an unsaturated fatty acid, more preferably an omega-3, omega-6, omega-7 or omega-9 unsaturated fatty acid, and further preferably an omega-7 unsaturated fatty acid. The term "omega-X unsaturated fatty acid" refers to an unsaturated fatty acid characterized by the presence of an unsaturated bond at the Xth bond from the methyl end of the fatty acid.

Feed (Feed Composition)

The feed (feed composition) of the present invention may include, for example, but is not limited to, a feed for livestock animals, such as cows, horses and pigs; a feed for poultry, such as chickens, quails, turkeys, ducks and geese; a feed for fish farming of fish and shells, such as young yellowtail, yellowtail, sea bream, shrimps, oysters and short-necked clam; and a feed for companion animals, such as dogs and cats. The feed for poultry is preferably for chickens, more preferably chickens, such as, but not limited to, broilers, layer hens, and locally raised chickens (Jidori chickens). The feed of the present invention can be produced or processed as appropriate by adding the lactic acid bacteria of the present invention and a fatty acid to a feed in accordance with a conventional production method for feeds.

Compositions for Enhancing IL-12 Production and for Immunostimulation

The composition of the present invention is advantageously characterized by an IL-12 production enhancing effect and/or an immunostimulatory effect as described above. The composition of the present invention may serve as a feed, but not limited thereto, and in another preferred example, the composition may serve as a food or a drink and/or a medicament (including a veterinary medicine). In a further preferred example, the composition of the present invention serves as an additive for a food or a drink.

The composition serving as a food or a drink, an additive for a food or a drink, or a medicament can be formulated into a pharmaceutical formulation by combining, as appropriate, the lactic acid bacteria with the fatty acid as described above and with a pharmaceutically acceptable carrier or additive. The formulation methods and formulation technology for preparing such a formulation are well established in the art, and the preparation of the formulation may be performed in accordance with such methods and technology. Specifically, for example, the composition serving as a medicament can be formulated into an oral formulation, such as a tablet, a coated tablet, a pill, a powder, granules, a capsule, a liquid, a suspension or an emulsion; or a parenteral formulation, such as an injection, an infusion, a suppository, an ointment or a patch. The blending ratio of the carrier or additive is determined as appropriate based on the amount of the carrier or additive usually used in the field of foods and drinks, medicaments or veterinary medicines. The carrier or additive that can be combined with the lactic acid bacteria and the fatty acid is not limited to a particular one, and examples thereof include, but are not limited to, various types of carriers, such as water, physiological saline, other aqueous solvents, or aqueous or oily bases; and various types of additives, such as enzymes, pH adjusting agents, preservatives, antimicrobial agents, antioxidants, antifungal agents, shelf life improvers, bleaching agents, brightening agents, fragrances, sweeteners, acidulants, seasonings, bittering agents, emulsifiers, thickeners, stabilizers, gelling agents, thickening agents, excipients, binders, disintegrants, lubricants, colorants, flavor improvers and fragrances. Techniques relating to such carriers or additives are well established in the art, and the carriers or additives can be used in accordance with such techniques.

When the composition for enhancing IL-12 production or the composition for immunostimulation according to the present invention is administered, the subject of the administration is preferably, but not limited to, a human or an animal, such as a livestock animal, a poultry bird or a companion animal, as described in the section "Feed (feed composition)."

When the composition of the present invention serves as a food or a drink, the food or drink includes health foods, foods with functional claims, foods for specified health use, and foods for sick people. The form of the food or drink is not limited to a particular one, and specific examples thereof include tablets, granules, powders, energy drinks, etc. that are ingested as so-called nutritional supplements or dietary supplements. Other examples thereof include, but are not limited to, drinks such as tea drinks, refreshing drinks, carbonated drinks, nutritional drinks, fruit juices, and lactic drinks; noodles such as buckwheat noodles, wheat noodles, Chinese noodles, and instant noodles; sweets and bakery products such as drops, candies, gum, chocolate, snacks, biscuits, jellies, jams, creams, pastries, and bread; fishery and livestock products, such as hams, sausages, hanpen fish cakes, and chikuwa fish cakes; dairy products such as processed milk and fermented milk; fats, oils and processed foods thereof, such as vegetable oils, oils for deep frying, margarine, mayonnaise, shortening, whipped cream, and dressings; seasonings such as sauces and dipping sauces; retort pouch foods such as curry, stew, rice-bowl cuisine, porridge, and rice soup; and frozen desserts, such as ice creams, and sherbets. Techniques relating to such foods and drinks are well established in the art, and the foods and drinks can be produced and used in accordance with such techniques.

Bacteriostatic Composition

The composition of the present invention is also preferably advantageously characterized by a bacteriostatic effect that inhibits bacterial growth. The bacteria that are inhibited by the bacteriostatic effect of the composition of the present invention preferably include, but are not limited to, bacteria that cause intestinal infections, for example, *Salmonella* spp., *Salmonella typhi*, and *Salmonella* paratyphi; pathogenic *Escherichia coli*, such as enterohemorrhagic *E. coli*, such as O-157, 0-111 and O-121, enterotoxigenic *E. coli* and enteroinvasive *E. coli; Vibrio cholerae, Shiga bacillus, Campylobacter, Clostridium, Staphylococcus aureus, Clostridium perfringens, Vibrio parahaemolyticus*, etc. Preferred examples of *Salmonella* spp. include, but are not limited to, *Salmonella typhi, Salmonella* paratyphi and *Salmonella enteritidis*.

The composition of the present invention may serve as a feed, but not limited thereto, and in another preferred example, the composition may serve as a food or a drink and/or a medicament (including a veterinary medicine).

The composition serving as a food or a drink, an additive for a food or a drink, or a medicament can be formulated into a pharmaceutical formulation by combining, as appropriate, the lactic acid bacteria with the fatty acid as described above and with a pharmaceutically acceptable carrier or additive. The formulation methods and formulation technology for preparing such a formulation are well established in the art, and the preparation of the formulation may be performed in accordance with such methods and technology. Specifically, for example, the composition serving as a medicament can be formulated into an oral formulation, such as a tablet, a coated tablet, a pill, a powder, granules, a capsule, a liquid, a suspension or an emulsion; or a parenteral formulation, such as an injection, an infusion, a suppository, an ointment or a patch. The blending ratio of the carrier or additive is determined as appropriate based on the amount of the carrier or additive usually used in the field of foods and drinks, medicaments or veterinary medicines. The carrier or additive that can be combined with the lactic acid bacteria and the fatty acid is not limited to a particular one, and examples thereof include, but are not limited to, various types of carriers, such as water, physiological saline, other aqueous solvents, or aqueous or oily bases; and various types of additives, such as enzymes, pH adjusting agents, preservatives, antimicrobial agents, antioxidants, antifungal agents, shelf life improvers, bleaching agents, brightening agents, fragrances, sweeteners, acidulants, seasonings, bittering agents, emulsifiers, thickeners, stabilizers, gelling agents, thickening agents, excipients, binders, disintegrants, lubricants, colorants, flavor improvers and fragrances. Techniques relating to such carriers or additives are well established in the art, and the carriers or additives can be used in accordance with such techniques.

When the composition of the present invention serves as a food or a drink, the food or drink includes health foods, foods with functional claims, foods for specified health use, and foods for sick people. The form of the food or drink is not limited to a particular one, and specific examples thereof include tablets, granules, powders, energy drinks, etc. that are ingested as so-called nutritional supplements or dietary supplements. Other examples thereof include, but are not limited to, drinks such as tea drinks, refreshing drinks, carbonated drinks, nutritional drinks, fruit juices, and lactic drinks; noodles such as buckwheat noodles, wheat noodles, Chinese noodles, and instant noodles; sweets and bakery products such as drops, candies, gum, chocolate, snacks, biscuits, jellies, jams, creams, pastries, and bread; fishery and livestock products, such as hams, sausages, hanpen fish cakes, and chikuwa fish cakes; dairy products such as processed milk and fermented milk; fats, oils and processed foods thereof, such as vegetable oils, oils for deep frying, margarine, mayonnaise, shortening, whipped cream, and dressings; seasonings such as sauces and dipping sauces; retort pouch foods such as curry, stew, rice-bowl cuisine, porridge, and rice soup; and frozen desserts, such as ice creams, and sherbets. Techniques relating to such foods and drinks are well established in the art, and the foods and drinks can be produced and used in accordance with such techniques.

Although the details of the mechanism are unknown, the bacteriostatic effect according to the present invention is exhibited by the administration of the feed or the composition of the present invention to a subject, probably in a manner that the feed or the composition enhances IL-12 production and/or stimulates an immune response, thereby inhibiting the growth of *Salmonella* spp. or other bacteria.

When the bacteriostatic composition of the present invention is administered, the subject of the administration is preferably, but not limited to, a human or an animal, such as a livestock animal, a poultry bird or a companion animal, as described in the section "Feed (feed composition)."

Other Ingredients

The feed or the composition of the present invention may further contain an ingredient known in the field of, for example, medicine, pharmaceuticals, veterinary medicine, foods, etc. to the extent that the effects of the present invention are not impaired.

Such an ingredient may be, for example, other lactic acid bacteria that have immunostimulation activity. For example, the feed or the composition of the present invention may further contain lactic acid bacteria belonging to the genus *Lactobacillus* other than *Lactobacillus plantarum* strain L-137 as described above, and/or lactic acid bacteria belonging to the genus *Streptococcus, Enterococcus, Lactococcus, Bifidobacterium*, etc. More specific examples of the lactic acid bacteria include, but are not limited to, *Lactobacillus plantarum, Lactobacillus acidophilus, Lactobacillus brevis, Lactobacillus casei, Lactobacillus fermentum, Lactobacillus paracasei, Lactobacillus buchneri, Lactobacillus delbrueckii*, or *Lactobacillus rhamnosus; Streptococcus thermophilus; Enterococcus faecalis*, or *Enterococcus faecium; Lactococcus lactis*, or *Lactococcus plantarum*; or *Bifidobacterium thermophilum, Bifidobacterium longum*, or *Bifidobacterium breve*; etc.

Dosage

The intake of *Lactobacillus plantarum* L-137, when administered orally or via an injection, can be determined depending on the age and body weight of the subject, the symptoms, the administration period, the dosage form, the mode of administration, a medicine to be co-administered, etc. For example, the intake of *Lactobacillus plantarum* L-137 based on the weight of the dried killed cells is preferably about 0.5 to 200 mg per adult human (about 60 kg) per day, more preferably about 1 to 100 mg per adult human (about 60 kg) per day, and further more preferably about 2 to 50 mg per adult human (about 60 kg) per day. The intake of *Lactobacillus plantarum* L-137 based on the number of the viable cells is preferably about $5 \times 10^8$ to $2 \times 10^{11}$ cfu (colony forming unit) per adult human (about 60 kg) per day, more preferably about $1 \times 10^9$ to $1 \times 10^{11}$ cfu per adult human (about 60 kg) per day. The frequency of intake may be once a day or multiple times a day.

When administered via external application, the amount of *Lactobacillus plantarum* L-137 applied may be appropriately selected depending on the area of the skin to be treated. Typically, the amount of *Lactobacillus plantarum* L-137 applied is preferably about 0.01 to 2.5 mg, more preferably about 0.02 to 1 mg, per day for about 10 cm$^2$ of the applied site. The daily dose may be administered or applied as a single dose per day or as multiple divided doses per day.

Production Methods

The present invention includes a method for producing the composition of the present invention which serves as a feed etc., the method comprising, for example, mixing *Lactobacillus plantarum* strain L-137 (*Lactobacillus plantarum* L-137) or a processed product thereof with a fatty acid and with, if desired, another ingredient. The mixing is preferably performed by mixing or stirring *Lactobacillus plantarum* strain L-137 (*Lactobacillus plantarum* L-137) or a processed product thereof with a fatty acid or a salt thereof and another ingredient by a known method or a method known per se in such a manner that all the ingredients are thoroughly homogeneous in the resulting feed or composition. The mixing or stirring methods are well established in the art, and the mixing or stirring may be performed in accordance with such methods.

Examination of IL-12 Production Enhancing Effect, Immunostimulating Effect and Bacteriostatic Effect The effects of the feed or the composition of the present invention can be confirmed by, for example, examining whether the feed or other types of compositions of the present invention comprising *Lactobacillus plantarum* strain L-137 (*Lactobacillus plantarum* L-137) or a processed product thereof and a fatty acid or a salt thereof are more effective in enhancement of IL-12 production, immunostimulation activity or bacteriostasis than a feed or a composition not comprising *Lactobacillus plantarum* strain L-137 (*Lactobacillus plantarum* L-137) or a processed product or a fatty acid or a salt thereof. Methods for examining IL-12 production and immunostimulating activity are well established in the art, including ELISA etc., and the examination may be performed in accordance with such methods. Methods for examining the bacteriostatic effect are also well established in the art, including observation of bacterial growth by visual or microscopic observation, examination of bacterial growth by culturing the bacteria on an appropriate culture medium, measurement of the amount of an enzyme produced by bacteria, PCR, etc. Examination of the bacteriostatic effect may be performed in accordance with such methods.

The immunostimulating activity specifically refers to, for example, but is not limited to, activity for enhancing the production of cytokines such as interleukins, e.g., IL-12, or interferons, e.g., IFN-β or IFN-γ, by cells such as B cells, T cells, macrophages, natural killer (NK) cells, or dendritic cells.

Examples of the examination methods are described in the Examples described later.

When the composition of the present invention is formulated into a food or a drink, a feed for an animal, a medicament (including a veterinary medicament) or a quasi-drug, these formulations or an package insert or a package box thereof may have an indication showing that the formulations contain lactic acid bacteria that have an IL-12 production enhancing effect or immunostimulating activity or a processed product thereof, based on the effects of the composition of the present invention.

The mass ratio of the lactic acid bacteria or a processed product thereof to the fatty acid or a salt thereof (lactic acid bacteria or a processed product thereof: fatty acid or a salt thereof) in the feed of the present invention is, for example, preferably 1:0.5 to 50000, more preferably 1:0.5 to 2000, further preferably 1:0.5 to 100, and particularly preferably 1:0.5 to 2.5.

The mass ratio of the lactic acid bacteria or a processed product thereof to the fatty acid or a salt thereof (lactic acid bacteria or a processed product thereof: fatty acid or a salt thereof) in the composition of the present invention including the medicament (the veterinary medicament), the food or the drink and the quasi-drug of the present invention is, for example, preferably 1:0.5 to 50000, more preferably 1:0.5 to 2000, further preferably 1:0.5 to 100, and particularly preferably 1:0.5 to 2.5.

EXAMPLES

The present invention will be described more specifically with reference to the following examples and experiments, but the present invention is not limited thereto.

Example 1: Examination of Enhanced IL-12
Production Promoting Effect when Lactic Acid
Bacteria of the Present Invention and a Fatty Acid
or a Salt Thereof are Added to an Immune Cell
Line Experimental Method Dried killed cells of *Lactobacillus plantarum* L-137 were suspended in PBS to 2 mg/mL, and diluted in RPMI 1640 medium containing 10% FBS to 40 μg/mL to give test liquid 1. A fatty acid (meddle-chain or long-chain) or a sodium salt of a fatty acid (short-chain) was dissolved in DNase-free water (for the short-chain fatty acid) or EtOH (for the meddle-chain or long-chain fatty acid) to 0.5 M, and diluted in RPMI 1640 medium containing 10% FBS to 400 μM to give test liquid 2. The macrophage-like cell line J774.1 cells (Cell No. JCRB9108; JCRB Cell Bank of the National Institutes of Biomedical Innovation, Health and Nutrition) were suspended in RPMI 1640 medium containing 10% FBS to a density of $1.0 \times 10^6$ cells/mL to give a cell line suspension. 100 μL of the cell line suspension was seeded in a 96-well culture plate together with 50 μL of the test liquid 1 or 2 (final concentration of the bacterial cells: 10 μg/mL, final concentration of the fatty acid: 100 μM, and final concentration of the macrophage-like cells: $5.0 \times 10^5$ cells/mL), and cultured in an incubator under 5% $CO_2$ at 37° C. for 48 hours. At the end of culture, the IL-12p40 levels in the supernatant were measured by ELISA. The detection limit of the ELISA assay was 0.07 ng/mL. The results are shown in Table 1 and FIGS. 1 and 2.

The trade names and the suppliers of the reagents used are as follows: sodium acetate (S5636, Sigma Aldrich®), sodium propionate (P5436, Sigma Aldrich®), N-sodium butyrate (B5887, Sigma Aldrich®), decanoic acid (21409, Sigma Aldrich®), palmitoleic acid (P9417, Sigma Aldrich®), FBS (fetal bovine serum SH30071.03, Hyclone®), RPMI 1640 medium (culture medium 23400-021, Thermo Fisher Scientific®), the primary antibody for ELISA (505202, Biolegend®), the secondary antibody for ELISA (BAF419, R&D Systems®), and a standard for ELISA (577009, Biolegend®).

TABLE 1

| Production of IL-12 (ng/ml) | Acetic acid | Propionic acid | Butyric acid | Decanoic acid | Palmitoleic acid |
|---|---|---|---|---|---|
| Addition of fatty acid alone | ND | ND | ND | ND | ND |
| Addition of L-137 alone | 0.280 | 0.443 | 0.190 | 0.530 | 0.498 |
| Co-addition of L-137 and fatty acid | 0.521 | 0.811 | 0.266 | 0.631 | 0.628 |

Results and Discussion

Figure 2:
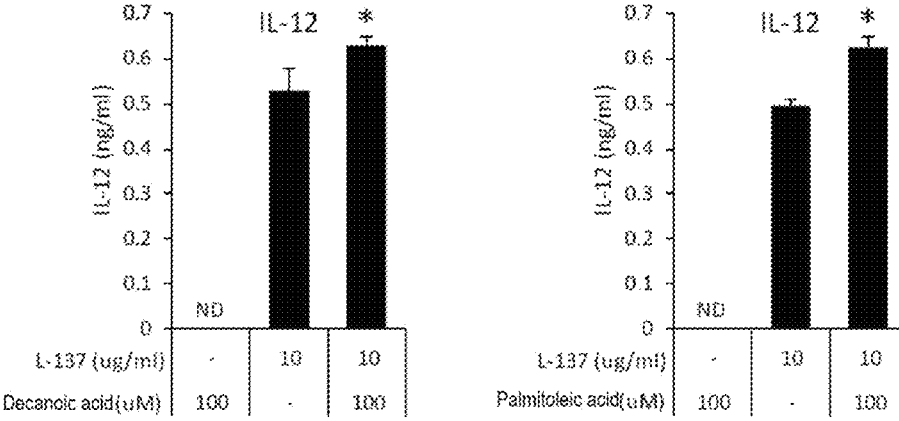
FIG. 2 shows the production of IL-12 by an immune cell line that received the lactic acid bacteria of the present invention alone, a fatty acid (a medium-chain fatty acid or a long-chain fatty acid) alone, or a combination of the lactic acid bacteria and the fatty acid. The asterisks (*) in the charts indicate that the p value of t-test between the addition of the lactic acid bacteria L-137 alone and the co-addition of the lactic acid bacteria L-137 and the fatty acid was $0.01 \leq p < 0.05$.

As shown in Table 1 above and FIGS. 1 and 2, when each of the fatty acids was added alone, neither of the fatty acids (the short-chain fatty acid, the medium-chain fatty acid or the long-chain fatty acid) nor the salt thereof could not enhance the production of IL-12 by the immune cells. The lactic acid bacteria *Lactobacillus plantarum* strain L-137 alone showed some enhancing effect on the production of IL-12 by the immune cells. In contrast, the lactic acid bacteria added together with each of the fatty acids significantly enhanced the production of IL-12, which was not observed at all when each of the fatty acids was added alone. The results demonstrate that the lactic acid bacteria used in combination with a fatty acid can enhance the production of IL-12. Enhanced production of IL-12 may have a positive impact on the immunostimulatory effect of the lactic acid bacteria.

The present invention is the first example of a fatty acid, which does not enhance the production of IL-12 alone, being found to significantly enhance IL-12 production when combined with the lactic acid bacteria *Lactobacillus plantarum* strain L-137.

Example 2: Examination of Enhanced IL-12 Production Promoting Effect and Bacteriostatic Effect when Lactic Acid Bacteria of the Present Invention and a Fatty Acid or a Salt Thereof are Given to Animals In this example, a feed (test food) containing *Lactobacillus plantarum* L-137 and a fatty acid was given to animals (broilers) and subjected to examination.

Experimental Method (1) Preparation of Tests and Breeding Method

In this example, broilers for meat (Ross 308, male, purchased from Charoen Pokphand Foods PCL., Lamphun, Thailand) were divided into the following test groups (T1, T2 and T3) of 64 birds and subjected to examination:

Test group T1 receiving a test diet (a powder feed) not containing a powder of dried killed bacterial cells of *Lactobacillus plantarum* L-137 or sodium propionate (100% Sodium Propionate, CALTECH CORPORATION LIMITED);

Test group T2 receiving a test diet mixed with dried killed bacterial cells of *Lactobacillus plantarum* L-137 at a concentration of 10 ppm; and Test group T3 receiving a test diet mixed with dried killed bacterial cells of *Lactobacillus plantarum* L-137 at 5 ppm and sodium propionate at 2000 ppm.

(In the experiments below, if the efficacy observed in T3 is equivalent or superior to that observed in T2, the test diet was considered to exhibit a synergistic effect.)

For each group, the test diet was given to the broilers from an age of 1 to 21 days, and then kept under normal diet from an age of 22 to 42 days. The ingredients of the test diets and the normal diet are shown in Table 2 below.

TABLE 2

| Ingredients | Age of 1-21 days | Age of 22-42 days |
| --- | --- | --- |
| Corn | 47.0 | 44.3 |
| Cassava powder | 11.0 | 15.0 |

TABLE 2-continued

| Ingredients | Age of 1-21 days | Age of 22-42 days |
| --- | --- | --- |
| Soybean meal | 28.0 | 20.0 |
| Extruded soybean | 3.0 | 4.0 |
| Fish meal (crude protein: 55%) | 4.0 | 5.0 |
| Rice bran | 5.0 | 10.0 |
| Calcium carbonate | 0.8 | 0.7 |
| Dicalcium phosphate (purity: 18%) | 0.3 | 0.0 |
| Salt | 0.3 | 0.3 |
| Premix*[1] | 0.5 | 0.5 |
| Mold inhibitor | 0.2 | 0.2 |
| Total | 100.0 | 100.0 |

*[1]Premix supplies the following per 100 kg diet: vitamin A: 12,000,000 IU, vitamin D: 2,400,000 IU, vitamin E: 30,000 IU, vitamin K: 1.2 g, vitamin B1: 2.0 g, vitamin B2: 6.0 g, vitamin B6: 3.0 g, vitamin B12: 20 mg, pantothenic acid: 10.0 g, nicotinic acid: 30 g, folic acid: 0.96 g, biotin: 125.0 mg, copper: 8.0 g, manganese: 61.0 g, iron: 80 g, zinc: 40.0 g, iodine: 850 mg and selenium: 300 mg.

(2) Examination of Enhanced IL-12 Production Promoting Effect

At an age of 42 days, the cecal tonsil was harvested from eight broilers from each group, and RNA was extracted. cDNA was synthesized from the RNA samples. Quantitative PCR was performed using the cDNA as a template. The primer sequences used for the PCR are shown in Table 3 below.

TABLE 3

| Gene | Primers (Forward) | Primers (Reverse) | PCR size | Accession No. |
| --- | --- | --- | --- | --- |
| IL-12 | TGTCTCACCTGC TATTTGCCTTAC (SEQ ID NO: 1) | CATACACATTCTCTC TAAGTTTCCACTGT (SEQ ID NO: 2) | 87 | NM_213571.1 |
| GAPDH | CCTCTCTGGCA AAGTCCAAG (SEQ ID NO: 3) | CATCTGCCCATTT GATGTTG (SEQ ID NO: 4) | 200 | V00407 |

Figure 3:
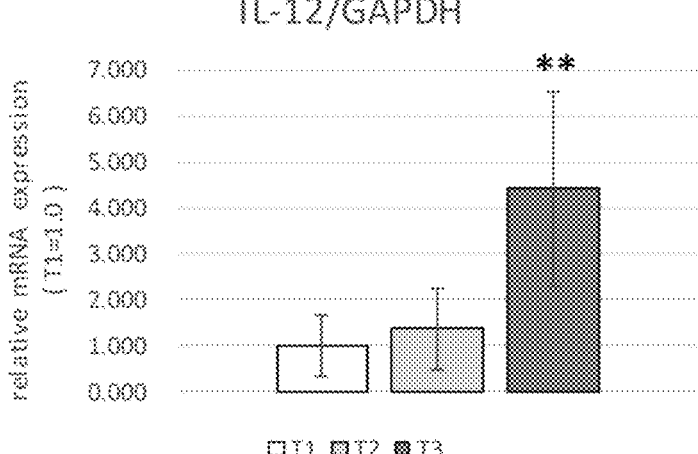
FIG. 3 shows the gene expression level of IL-12 when broilers were fed a feed comprising the lactic acid bacteria of the present invention alone, a fatty acid or a salt thereof alone, or a combination of the lactic acid bacteria and the fatty acid or a salt thereof. The asterisks (**) in the chart indicate that the p value of t-test between the T1 and T3 groups was $p < 0.01$.

Gene expression analysis was performed on the harvested cecal tonsil to determine the gene expression level of IL-12 in the broilers of the T1, T2 and T3 groups, and the results were summarized. The results are shown in FIG. 3 and Table 4 below.

TABLE 4

| IL-12 (normalized to T1 = 1.00) | Expression level | TTEST vs. T1 |
| --- | --- | --- |
| T1 | 1.00 ± 0.67 | |
| T2 | 1.37 ± 0.87 | 0.359 |
| T3 | 4.42 ± 2.11 | 0.002 |

(3) Examination of Bacteriostatic Effect on *Salmonella* Bacteria (*Salmonella* Spp.)

At an age of 42 days, the cecal content was aseptically harvested from six broilers from each group, and the number of *Salmonella* bacteria was counted. The results are shown in Table 5. The values in the table are the mean values.

TABLE 5

| *Salmonella* spp. | $(\log_{10} \text{cfu/g})$ |
| --- | --- |
| T1 | 6.8 |
| T2 | 7.1 |
| T3 | 6.0 |

Results and Discussion

The gene expression analysis in the cecal tonsil (FIG. 3 and Table 4) demonstrated that the gene expression level of IL-12 was significantly higher in the T3 group than in the T2 group. The number of *Salmonella* bacteria (*Salmonella* spp.) in the cecal content harvested from the broilers was smaller in the T3 group than in the T2 group.

These results indicate that a synergistic enhancing effect on IL-12 expression and a synergistic bacteriostatic effect were exhibited in the broilers that received the feed containing both of the dried killed bacterial cells of *Lactobacillus plantarum* L-137 and propionic acid. Although the details of the mechanism are unknown, the bacteriostatic effect is exhibited by the administration of the dried killed bacterial cells of *Lactobacillus plantarum* L-137 together with sodium propionate, probably in a manner that the co-administration of the dried killed bacterial cells and sodium propionate enhances IL-12 production in the host broilers, thereby inhibiting the growth of *Salmonella* bacteria.

The number of *Salmonella* bacteria (Table 5) indicated that a composition comprising the lactic acid bacteria *Lactobacillus plantarum* strain L-137 or a processed product thereof and a fatty acid or a salt thereof is effective for enhancing IL-12 production and for immunostimulation not only in vitro but also in animals (in vivo).

INDUSTRIAL APPLICABILITY

The feed and composition of the present invention have an IL-12 production enhancing effect, an immunostimulatory effect or a bacteriostatic effect, and are therefore useful as a food or a drink, a feed, a medicament or a quasi-drug, a cosmetic, etc.

The invention claimed is:

1. A feed comprising *Lactobacillus plantarum* strain L-137 as deposited as Accession Number: FERM BP-8607 or a culture thereof and a fatty acid or a salt thereof, wherein the *Lactobacillus plantarum* strain L-137 is killed, and wherein the fatty acid is at least one selected from the group consisting of formic acid, acetic acid, propionic acid, butyric acid, isobutyric acid, valeric acid, isovaleric acid, pyruvic acid, caproic acid, succinic acid and decanoic acid.

2. The feed according to claim 1, wherein the fatty acid is at least one selected from the group consisting of acetic acid, propionic acid, butyric acid, isobutyric acid, valeric acid, isovaleric acid, pyruvic acid, caproic acid and succinic acid.

3. The feed according to claim 1, wherein the amount of the *Lactobacillus plantarum* strain L-137 or a culture thereof contained in the feed is 0.0001 to 0.1% by mass relative to the total mass of the feed.

4. The feed according to claim 1, wherein the mass ratio of the *Lactobacillus plantarum* strain L-137 or a culture thereof to the fatty acid or a salt thereof in the feed is 1:0.5 to 50000.

5. The feed according to claim 2, wherein the amount of the *Lactobacillus plantarum* strain L-137 or a culture thereof contained in the feed is 0.0001 to 0.1% by mass relative to the total mass of the feed.

6. The feed according to claim 2, wherein the mass ratio of the *Lactobacillus plantarum* strain L-137 or a culture thereof to the fatty acid or a salt thereof in the feed is 1:0.5 to 50000.

7. The feed according to claim 3, wherein the mass ratio of the *Lactobacillus plantarum* strain L-137 or a culture thereof to the fatty acid or a salt thereof in the feed is 1:0.5 to 50000.

* * * * *